(12) United States Patent
Ryu

(10) Patent No.: US 12,285,280 B2
(45) Date of Patent: Apr. 29, 2025

(54) APPARATUS FOR DISPLAYING AIMING LIGHT IN HAND-HELD X-RAY DEVICE

(71) Applicant: DEXCOWIN CO., LTD., Seoul (KR)

(72) Inventor: Seung Bum Ryu, Seoul (KR)

(73) Assignee: DEXCOWIN CO., LTD., Seoul (KR)

( * ) Notice: Subject to any disclaimer, the term of this patent is extended or adjusted under 35 U.S.C. 154(b) by 232 days.

(21) Appl. No.: 18/163,094

(22) Filed: Feb. 1, 2023

(65) Prior Publication Data

US 2023/0248326 A1  Aug. 10, 2023

(30) Foreign Application Priority Data

Feb. 7, 2022 (KR) .................. 10-2022-0015786

(51) Int. Cl.
*A61B 6/08* (2006.01)
*A61B 6/00* (2006.01)
*A61B 6/51* (2024.01)

(52) U.S. Cl.
CPC .............. *A61B 6/08* (2013.01); *A61B 6/4405* (2013.01); *A61B 6/51* (2024.01)

(58) Field of Classification Search
CPC .... A61B 6/00; A61B 6/06; A61B 6/08; A61B 6/51; A61B 6/4405
See application file for complete search history.

(56) References Cited

FOREIGN PATENT DOCUMENTS

| JP | 2015112391 A | | 6/2015 | |
|---|---|---|---|---|
| KR | 20080094968 A | * | 10/2008 | ............... A61B 6/00 |
| KR | 101404004 B1 | | 6/2014 | |
| KR | 1020190080799 A | | 7/2019 | |
| KR | 1020210122985 A | | 10/2021 | |
| WO | WO-2021201355 A1 | * | 10/2021 | ............... A61B 6/08 |

* cited by examiner

*Primary Examiner* — Jurie Yun
(74) *Attorney, Agent, or Firm* — Rabin & Berdo, P.C.

(57) ABSTRACT

Apparatus for displaying aiming light in a hand-held X-ray device including an X-ray irradiation part (100), an upper cover (200), a lower cover (300), a lower support (400), and an aiming light guide (500) includes: an emission hole (600) through which LED light emitted along the aiming light guide (500) is transmitted; a shield plate (700) blocking an X-ray reflected by a subject; and a front cover (800) adjusting and aligning the aiming light emitted onto the subject, so as to accurately align the aiming light to an X-ray irradiation area.

7 Claims, 4 Drawing Sheets

APPARATUS FOR DISPLAYING AIMING LIGHT IN HAND-HELD X-RAY DEVICE

CROSS-REFERENCE TO RELATED APPLICATIONS

This U.S. non-provisional patent application claims priority under 35 U.S.C. § 119 of Korean Patent Application No. 10-2022-0015786, Feb. 7, 2022, the entire contents of which are hereby incorporated by reference.

TECHNICAL FIELD

The present invention relates to an apparatus for displaying aiming light in a hand-held X-ray device.

The aiming light may refer to a LED device disposed in an emission hole of an X-ray device and displaying an area irradiated with an X-ray, and since the hand-held X-ray device has a narrow internal structure, the present invention may accurately irradiate a subject with an X-ray by simply mounting a LED for the aiming light in the emission hole instead of adopting a complex collimator structure using a reflection mirror or an aperture and adjusting and aligning an LED irradiation area of the aiming light by a user before the X-ray is irradiated.

BACKGROUND ART

An X-ray beam is necessary to be aligned onto a center of a sensor heading perpendicularly to a subject and obtaining an image. When this alignment is not observed, cone-cut is generated. Since X-ray exposure of a cut portion of the cone-cut is small, the cut portion is shown as a transparent area in radiograph after processing. When a digital image is used, the cone-cut area is shown as being opaque or in a white color.

According to apparatus for display of X-ray photographing area of portable type (Korean Patent Registration No. 10-1404004 (announced on Jun. 13, 2014), an apparatus for display of an X-ray photographing area of a portable type, which displays, on a screen, an irradiation area of an X-ray irradiated through an X-ray oscillation part including an X-ray tube emitting an X-ray, a high-voltage generation part applying a high voltage to the X-ray tube, and an X-ray control part controlling the high-voltage generation part includes:

a subject image acquisition part that acquires a subject image for an X-ray irradiation range photographed by the X-ray oscillation part;

a liquid crystal display part that displays, in real time, a subject image, an X-ray photographing range, a distance to an X-ray irradiation position, an X-ray absorbed dose, and a photographed X-ray image, which are acquired through the subject image acquisition part;

a distance measurement part that measures a distance from the X-ray tube to the X-ray irradiation position; and a main control part for outputting an image displaying an X-ray irradiation restriction range in the subject image acquired through the subject image acquisition part through the liquid crystal display part and calculating and displaying, on the liquid crystal display part, the X-ray skin absorbed dose of an examinee according to the X-ray irradiation conditions.

Also, according to a portable X-ray imaging system (Korean Patent Publication No. 10-2019-80799 (published on Jul. 8, 2019)), provided is a portable X-ray imaging system including: an X-ray tube inserted into a body; and a detector disposed outside the body and receiving an X-ray emitted from the X-ray tube, and the X-ray tube includes: a filament emitting electrons when a voltage is applied; a base fixing the filament and including two filament through-holes to connect a power to both poles of the filament; a cylindrical extractor that is in close contact with the base and surrounds the filament without contacting the filament; a cutoff voltage providing part applying a cutoff voltage between the extractor and one pole of the filament; a target receiving the electrons emitted from the filament and emitting an X-ray; a body made of a ceramic material, which has one side connected with the filament and the other side connected with the target to form a sealed state between the filament and the target; an extraction pipe passing through the target and extracting air in the body to form a vacuum state; and a cap that is in close contact with the target at a side opposite to the body and surrounds an end of the extraction pipe.

RELATED ART DOCUMENT

Patent Document (Patent document 0001) Korean Patent Registration No. 10-1404004 (announced on Jun. 13, 2014)

(Patent document 0002) Korean Patent Publication No. 10-2019-80799 (published on Jul. 8, 2019)

DISCLOSURE OF THE INVENTION

Technical Problem

A sensor for acquiring an image of a subject may be fixed by a sensor holder and inserted into an oral cavity. Here, a user may assume an end of the sensor holder as a range containing the sensor and align a hand-held X-ray device with the subject on a straight line to perform X-ray photographing.

However, in addition to inconvenience in use due to a size and a weight of the sensor holder, human side effects may occur due to long-term X-ray exposure such as a long X-ray irradiation time because of a long distance to the subject from the hand-held X-ray device.

Also, the hand-held X-ray device has a difficulty in that a collimator is difficult to be mounted in an emission hole.

A typical X-ray collimator has an own weight more than 2 kg and a volume that is difficult to be mounted in the emission hole.

The hand-held X-ray device has an own weight around 1.5 kg to 2.5 kg, and when a typical heavy aperture-type collimator is added, portability as a hand-held device is reduced.

The hand-held X-ray device is recommended to obtain a best image at a distance of 5 cm or 2 inches from an end of the emission hole to the subject. When an additional collimator having a large volume is mounted to a front side of the emission hole, the device may be deviated from the distance for obtaining the best image.

Also, since the hand-held X-ray device is manipulated by hands of the user instead of being fixed to a fixed cradle when an X-ray picture of the subject is photographed, a photographed portion of the subject may be inaccurately photographed.

For example, in case of photographing teeth as shown in FIG. 1, when the hand-held X-ray device is rotated by a to the left due to movement of the hands of the user or the subject, a picture that is rotated by a to the right and is not leveled while a portion of the teeth is cut as shown in FIG. 2 may be obtained.

Technical Solution

The present invention provides an apparatus having a simple structure, which is capable of adjusting, aligning, and displaying aiming light with respect to a subject, in a hand-held X-ray device.

The present invention includes a rectangular collimator disposed outside an emission hole and capable of adjusting and aligning a display area of aiming light instead of having a complex collimator structure using a reflection mirror or an aperture to accurately display an X-ray irradiation area because a hand-held X-ray device has a narrow internal structure.

Advantageous Effects

The apparatus for displaying the aiming light in the hand-held X-ray device according to the present invention may allow the X-ray beam emitted onto the subject and the image sensor to be accurately perpendicularly aligned.

The apparatus for displaying the aiming light in the hand-held X-ray device according to the present invention may provide the lightweight portability with the simple structure to easily carry and conveniently use the X-ray device.

MODE FOR CARRYING OUT THE INVENTION

Figure 1:
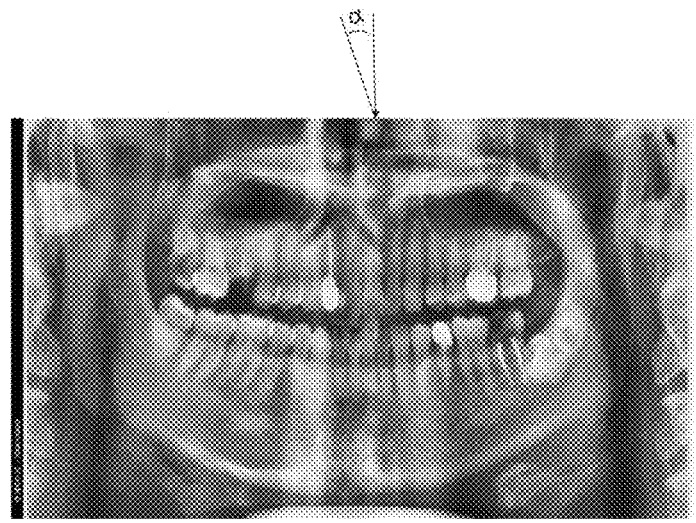
FIG. 1 is a view illustrating an embodiment in which a hand-held X-ray device is rotated by a to the left.
Figure 2:
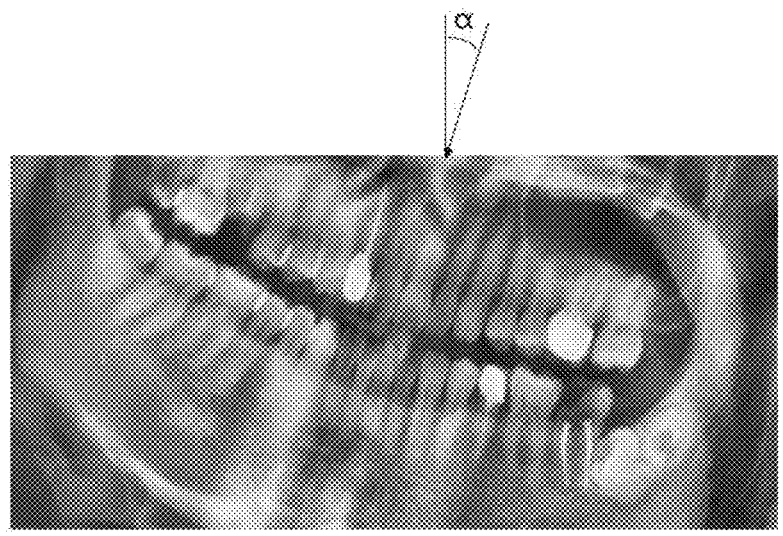
FIG. 2 is a view illustrating an embodiment in which some of teeth are cut and are not horizontally aligned.

Since the present invention may have diverse modified embodiments, preferred embodiments are illustrated in the drawings and are described in the detailed description of the invention. However, this does not limit the present invention within specific embodiments and it should be understood that the present invention covers all the modifications, equivalents, and replacements within the idea and technical scope of the present invention.

In the following description, the technical terms are used only for explaining a specific exemplary embodiment while not limiting the present invention. The terms of a singular form may include plural forms unless referred to the contrary.

Hereinafter, an embodiment of the present invention will be described in detail with reference to the accompanying drawings.

Figure 3:
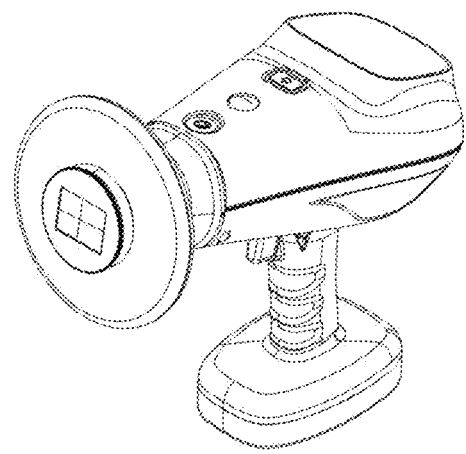
FIG. 3 is a perspective view of the present invention.
Figure 4:
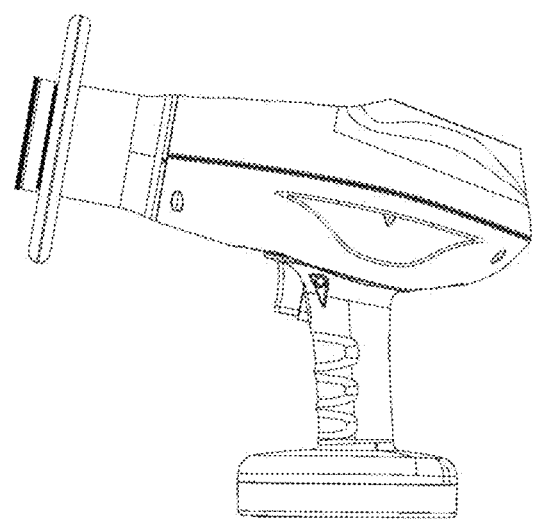
FIG. 4 is a side view of the present invention.

FIGS. 3 and 4 are perspective view and a side view of a hand-held X-ray device according to the present invention.

While the hand-held X-ray device is conveniently carried, the hand-held X-ray device may not accurately perform alignment between an X-ray beam and a subject when photographing without a fixed cradle.

Figure 5:
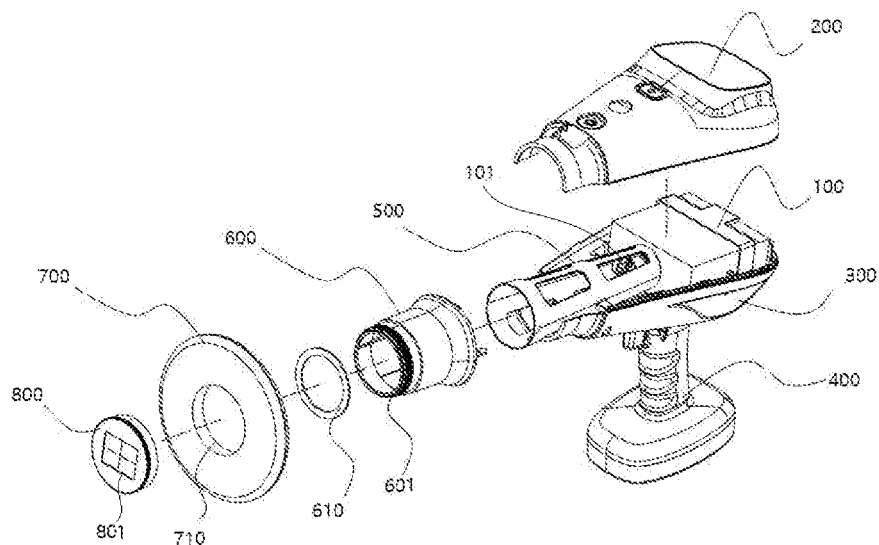
FIG. 5 is an exploded perspective view of the present invention.

Thus, the present invention proposes a unit for adjusting and aligning aiming light, which is capable of displaying an X-ray irradiation area in advance at a frontmost portion of an emission hole of an X-ray beam as with the hand-held X-ray device in FIGS. 3 to 5.

FIG. 5 is an exploded perspective view of the hand-held X-ray device according to the present invention. The hand-held X-ray device according to the present invention includes an X-ray irradiation part 100, LED (101), an upper cover 200, a lower cover 300, a lower support 400, and an aiming light guide 500.

A power button of the device and an aiming light operation button may be disposed on the upper cover 200, and when alignment of the aiming light is accurately completed, the X-ray may be irradiated by pulling a handle lever attached to the lower support 400.

Preferably, the aiming light operation button may be disposed at a button applicable position on the lower cover 300, the lower support 400, the aiming light guide 500, and the emission hole 600 in addition to the upper cover 200.

Also, the aiming light may be initially operated by pulling the handle lever attached to the lower support 400, and when the alignment is completed, the X-ray may be irradiated by pulling the handle lever attached to the lower support 400 again.

Before the X-ray is emitted from the X-ray irradiation part 100, LED light emitted along the aiming light guide 500 is transmitted to the emission hole 600.

The emission hole 600 passes through an opened surface 710 of a shield plate 700 that blocks the X-ray reflected by the subject and is coupled with the front cover 800.

A screw thread 601 formed at a front end of the emission hole 600 is screwed into a screw groove 841 formed in an inner surface of the front cover 800, and the emission hole 600 passes through the opened surface 710 of the shield plate 700 and is fitted thereto.

Preferably, the emission hole 600 includes a contact ring 610, and the contact ring 610 allows the front cover 800 and the emission hole 600 to completely contact each other without an empty space therebetween when the front cover 800 is coupled with the emission hole 600. The contact ring 610 is made of soft solder that is easily processed.

The front cover 800 adjusts and aligns the X-ray irradiation area by rotating the rectangular collimator 801 to accurately display the X-ray irradiation area while checking the aiming light emitted onto the subject with naked eyes.

Figure 6:
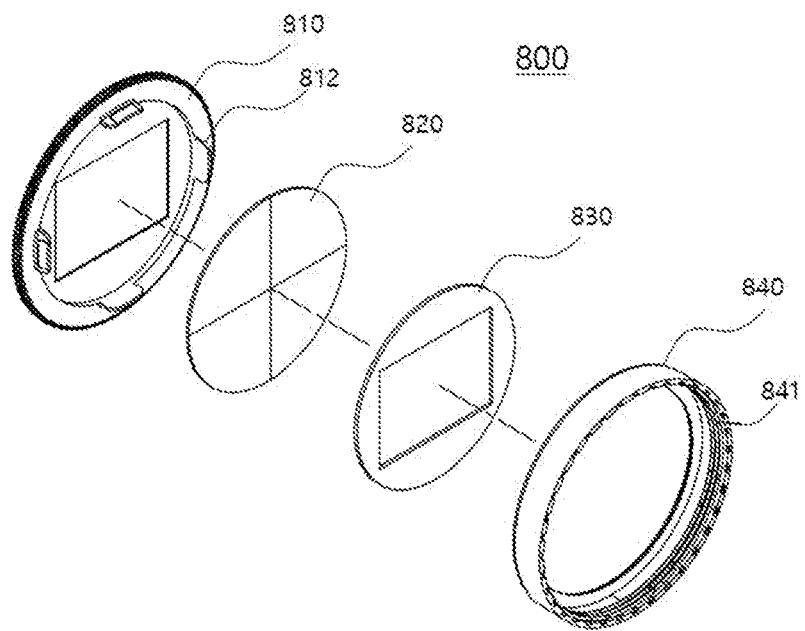
FIGS. 6 and 7 are exploded perspective views of a front cover.

As illustrated in FIG. 6, the front cover 800 includes a front transmission window 810, a cross printing plate 820, a rectangular transmission plate 830, and a cylindrical case 840. A plurality of hooks 812 are disposed in the front transmission window 810, and the hooks 812 are coupled to an inner surface of an edge of the cylindrical case 840 to couple the front transmission window 810 and the cylindrical case 840.

The cross printing plate 820 is a transparent plate made of an acrylic material printed so that a cross mark may be displayed when the subject is irradiated with the aiming light. The rectangular transmission plate 830 induces the aiming light and the X-ray to be emitted onto the subject in a square shape and is made of soft solder that is easily processed.

The cylindrical case 840 has a screw groove 841 formed at the inner surface of the edge thereof to be screwed with the screw thread 601 formed at the front end of the emission hole 600 and is hooked to the front transmission window 810.

The front transmission window 810, the cross printing plate 820, and the rectangular transmission plate 830 may be integrally rotated when the front transmission window 810 is rotated in accordance with the subject by attaching surfaces thereof to each other. Here, although the front transmission window 810 is rotated simultaneously with the cross printing plate 820 and the rectangular transmission plate 830, the cylindrical case 840 is coupled so as not to be rotated.

Figure 7:
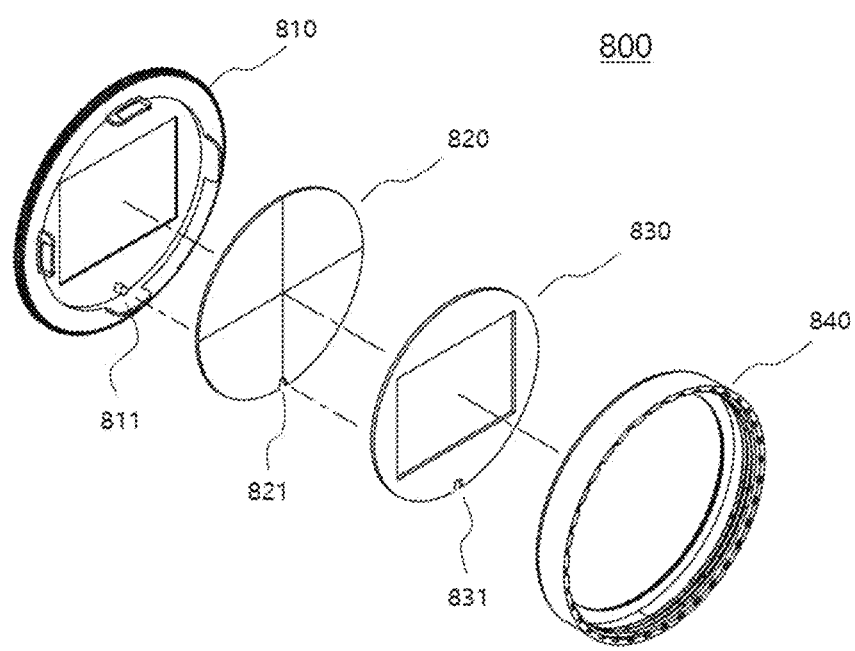

Preferably, as illustrated in FIG. 7, as a rotation projection 811 is disposed on the front transmission window 810, a rotation groove a 821 is defined in the cross printing plate 820, and a rotation groove b 831 is defined in the rectangular transmission plate 830, the rotation projection 811 may be coupled with the rotation groove a 821 and the rotation groove b 831.

When the above-described coupling is performed, the front transmission window 810, the cross printing plate 820, and the rectangular transmission plate 830 may be integrally rotated when the front transmission window 810 is rotated in accordance with the subject even without attaching the surfaces thereof to each other.

Preferably, the present invention may further include a well-known coupling structure capable of integrally rotating the front transmission window 810, the cross printing plate 820, and the rectangular transmission plate 830 as described above.

When the aiming light of the rectangular collimator 801 is accurately aligned with the X-ray irradiation area, photographing is performed by irradiating the X-ray from the X-ray irradiation part 100.

The invention claimed is:

1. Apparatus for displaying aiming light in a hand-held X-ray device comprising an X-ray irradiation part (100), an upper cover (200), a lower cover (300), a lower support (400), and an aiming light guide (500), comprising:

an emission hole (600) through which LED light emitted along the aiming light guide (500) is transmitted, wherein a LED (101) is disposed in the emission hole (600) for emitting the LED light;

a shield plate (700) configured to block an X-ray reflected by a subject; and a front cover (800) configured to adjust and align the aiming light emitted onto the subject, wherein the aiming light is accurately aligned to an X-ray irradiation area, wherein the front cover (800) comprises a front transmission window (810), a cross printing plate (820), a rectangular transmission plate (830), and a cylindrical case (840).

2. The apparatus of claim 1, wherein the emission hole (600) passes through an opened surface (710) of the shield plate (700) and is coupled with the front cover (800).

3. The apparatus of claim 1, wherein a screw thread (601) formed at a front end of the emission hole (600) is screwed into a screw groove (841) formed in an inner surface of the front cover (800), and the emission hole (600) passes through an opened surface (710) of the shield plate (700) and is fitted thereto.

4. The apparatus of claim 1, wherein the front cover (800) adjusts and aligns the X-ray irradiation area by rotating a rectangular collimator (801) to accurately display the X-ray irradiation area while checking the aiming light emitted onto the subject with naked eyes.

5. The apparatus of claim 1, wherein hooks (812) disposed in the front transmission window (810) are coupled to an inner surface of an edge of the cylindrical case (840) to couple the front transmission window (810) and the cylindrical case (840).

6. The apparatus of claim 1, wherein the cylindrical case (840) has a screw groove (841) formed at an inner surface of an edge thereof to be screwed with a screw thread (601) formed at a front end of the emission hole (600).

7. The apparatus of claim 1, wherein the front transmission window (810), the cross printing plate (820), and the rectangular transmission plate (830) are integrally rotated when the front transmission window (810) is rotated in accordance with the subject.

\* \* \* \* \*